(12) United States Patent
Zygmont

(10) Patent No.: US 6,488,646 B1
(45) Date of Patent: *Dec. 3, 2002

(54) SWAB DELIVERABLE ACTIVES

(75) Inventor: Joseph Frank Zygmont, Killingworth, CT (US)

(73) Assignee: Unilever Home & Personal Care USA, Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/950,855

(22) Filed: Sep. 12, 2001

(51) Int. Cl.$^7$ .............................................. A61M 35/00
(52) U.S. Cl. ............................................................ 604/1
(58) Field of Search ........................................ 604/1–3

(56) References Cited

U.S. PATENT DOCUMENTS

| | | |
|---|---|---|
| 1,822,567 A | 9/1931 | Davies |
| 2,006,539 A | 7/1935 | Deford |
| 2,680,701 A | 6/1954 | Cusumano |
| 2,809,149 A | 10/1957 | Cusumano |
| 2,987,063 A | 6/1961 | Glickston |
| 3,343,540 A | 9/1967 | Siegel et al. |
| 4,022,880 A | 5/1977 | Vinson et al. |
| 4,718,889 A | 1/1988 | Blasius, Jr. et al. |
| 4,767,398 A | 8/1988 | Blasius, Jr. |
| 4,795,421 A * | 1/1989 | Blasius, Jr. et al. ............. 604/1 |
| 4,887,994 A | 12/1989 | Bedford |
| 5,035,348 A | 7/1991 | Seifert |
| 5,061,689 A | 10/1991 | Alvarez |
| 5,100,028 A | 3/1992 | Seifert |
| 5,676,643 A | 10/1997 | Cann et al. |
| 5,846,215 A | 12/1998 | Zygmont |
| 5,919,152 A | 7/1999 | Zygmont |

* cited by examiner

Primary Examiner—Dennis Ruhl
(74) Attorney, Agent, or Firm—Milton L. Honig

(57) ABSTRACT

A swab product is provided which includes a swab defined by an elongate stem and a fibrous absorbent covering such as cotton on at least one end of the stem. The fibrous absorbent covering is held together by a film-forming polymer. A treatment agent is provided which includes an active agent in a carrier. Particularly preferred is a highly viscous hydrophobic treatment composition such as petrolatum serving as a carrier for actives such as bacitracin ointment.

9 Claims, 1 Drawing Sheet

SWAB DELIVERABLE ACTIVES

BACKGROUND OF THE INVENTION

1. Field of the Invention

The invention concerns swabs impregnated with physiologically active agents and a related method for topically treating skin, hair and the oral cavity.

2. The Related Art

Swabs having an absorbent covering on the tip and an elongated stem are well known. Cotton is generally used as the absorbent covering material. Stem materials are often of wood, rolled paper or plastic. An adhesive binder may be used to more firmly hold the absorbent covering in place upon the swab. Ordinarily extremely small amounts of binder are used so as not to interfere with the billowy nature of the attached cotton.

Swabs have been used as applicators for a variety of cosmetic and pharmaceutical purposes. Rarely are they pretreated with any sort of agent intended for transfer. It is up to the consumer to dip the swab into a particular agent or cosmetic which they wish to apply to their body. Non-pretreatment of swabs has the advantage of universality and allows choice to the consumer. Unfortunately, universality sacrifices the advantage of convenience. Perhaps even more important is sacrifice of the functional advantage from a swab engineered to solve a particular problem.

U.S. Pat. No. 5,035,348 and U.S. Pat. No. 5,100,028, both to Seifert and assigned to the Institute Guilfoyle, disclose an engineered swab-type article intended for delivery of liquid products to the skin. Therein is disclosed a flexible stick-like fluid dispenser mounted with a cotton tip. A frangible seal separates the fluid compartment from the tip. Upon application of force against the seal, a separation wall breaks allowing fluid to permeate the cotton tip. Products related to this technology are sold by the Purdue Frederick Company under the trademark Betadine® Prep Stick. This product is described as a self-saturating disposable swab applicator for povidone-iodine used as a topical antiseptic. The Betadine® Prep Stick applicator is marketed as an individual swab sealed within a tear open pouch. Systems of this type are expensive to manufacture, and somewhat messy considering the requirement for the active agent to be delivered in a relatively non-viscous highly fluid carrier. Active agents must also be soluble in that carrier for transfer to the tip.

U.S. Pat. No. 5,846,215 and U.S. Pat. No. 5,919,152 to Zygmont disclose a swab whose absorbent covering has been treated for resistance to bacterial contamination. The covering, in particular a cotton wad, is dipped into a padding medium which includes an anti-microbial agent dispersed in a water slurry having up to 20% of a binder. The swab is dried after the padding step resulting in the anti-microbial agent being deposited in dry form onto the cotton wad.

A particular problem in transference of active agents occurs where the transferred composition is a relatively viscous substance. Fibers of the cotton tend to adhere to the viscous composition causing clumps of fibers to transfer with the composition onto the body. Not only is deposition of fibers onto the skin aesthetically and functionally displeasing, but transfer of the composition as a non-messy, accurate application is thereby hindered.

Accordingly, it is an object of the present invention to provide a swab pretreated with an active agent for topical application to the body.

Another object of the present invention is to provide a cotton swab pretreated with an active agent forming an applicator system that can cleanly deliver the agent without interference and transfer of any substantial amount of cotton from the applicator tip.

SUMMARY OF THE INVENTION

A swab product is provided which includes:

(i) an elongate stem with first and second ends opposite one another, a fibrous absorbent covering surrounding at least one of the first and second ends, the covering being held together by a film-forming polymer; and (ii) a treatment composition including an active agent, the composition having a viscosity ranging from about 50 cps to about 5,000,000 cps.

In a more particular aspect of the present invention, there is provided a swab product including:

(i) an elongate stem with first and second ends opposite one another, fibrous cellulosic absorbent covering surrounding at least one of the first and second ends, the cotton being held together by a film-forming polymer in an effective amount to prevent the fibrous covering from unfurling during use; and (ii) a treatment composition including from about 0.0000001 to about 20% by weight of the composition of an active agent and from about 80 to about 99.9% by weight of a composition of a hydrophobic cosmetically acceptable carrier, the composition having a viscosity ranging from about 100,000 cps to about 3,500,000 cps.

Still further, there is provided a method for treating diseased or injured skin by applying through aid of a swab, a treatment composition including an effective amount of an active agent against the disease or injury suspended in a cosmetically acceptable carrier, the composition having a viscosity ranging from about 50 to about 5,000,000 cps, the swab including an elongate stem with first and second ends opposite one another, an absorbent covering such as cotton surrounding at least one of the first and second ends, the covering being held together by a film-forming polymer and whereupon is deposited the treatment composition.

BRIEF DESCRIPTION OF THE DRAWING

Further objects, features and advantages of the present invention will become more readily apparent from consideration of the drawing which consists of a sole Figure showing in cross section a swab within a seated pouch.

BRIEF DESCRIPTION OF THE INVENTION

Figure 1:
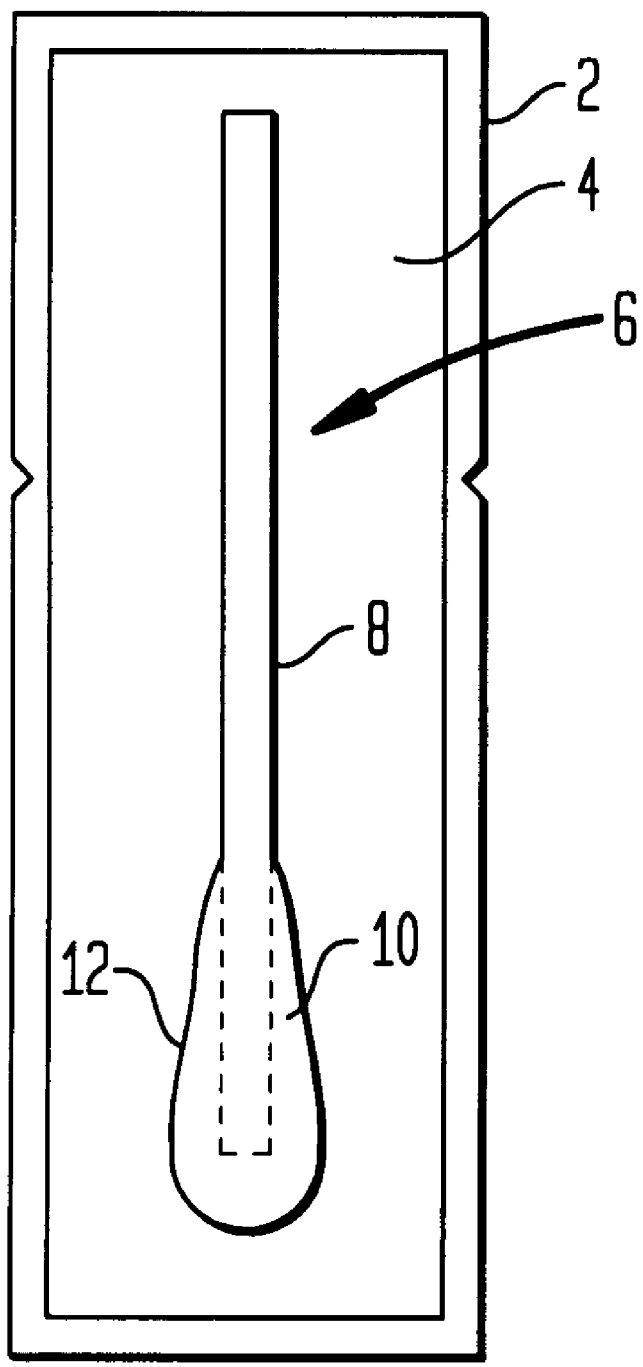

Now it has been found that fibrous absorbent coverings such as cotton or rayon can maintain their integrity by impregnation with a film-forming polymer.

Furthermore, treatment compositions deposited on the fibrous covering can be transferred to a human body surface with less concern. Transfer will no longer be inhibited by the composition adhering more to the fibrous absorbent than to the body surface intended for treatment. No longer will any substantial amount of cotton separate from the covering wad through binding more strongly to the transferred viscous treatment composition.

The Figure illustrates a sealed pouch 2 with interior cavity 4 revealed to show a swab 6. Constituents of the swab include a stem 8 and a fibered absorbent covering 10 at a first end of the stem. A treatment composition 12 with a bacitracin ointment is delivered within an oleaginous carrier of mineral oil/petrolatum.

Stems of the present invention can be formed from natural and synthetic materials. Among the natural materials are cellulosics such as rolled paper and wood. Suitable synthetic materials for the stems include a variety of plastics such as polystyrene, polypropylene, polyethylene, polyamides, polyester and polyvinyl chloride. Most preferred are polystyrene, polypropylene and polyethylene. When the treatment composition has a hydrophobic carrier such as mineral oil and/or petrolatum, cellulosic or wood materials are not preferred because adhesives and other substances within the cellulosic tend to break down during long periods of contact.

Fibered absorbent coverings may be derived from natural or synthetic fibers. Cellulosics are the preferred natural fibered absorbent. Cotton, rayon and mixtures thereof are most preferred. Other types of fibered wads may also be employed. Particularly useful are Fibered polypropylene, polyethylene, polyester and polyamide.

Film-forming polymers of the present invention may be selected from nonionic, anionic, cationic and amphoteric polymers.

Examples of nonionic polymers suitable for film-forming purposes are the copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1:1) wherein such copolymers are 50% esterified with a saturated alcohol containing from 1 to 4 carbon atoms such as ethanol or butanol; and acrylic polymers containing acrylic acid or methacrylic acid or their esters with one or more saturated alcohols having from 1 to 22 carbon atoms such as methyl methacrylate, ethyl acrylate, ethyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerized terpolymer of methacrylic acid, n-butyl acrylate and ethyl acrylate (e.g., in a weight percent ratio of 31:42:27, respectively).

Further examples of nonionic film-forming polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 under the trademark PVP K-90 and those having an average molecular weight of about 1,000,000 sold under the trademark of PVP K-120. Particularly preferred is poly(methyl vinyl ethertmaleic anhydride) as an unneutralized resin available from ISP Corporation under the trademark Gantrez® S-97 BF.

Anionic film-forming polymers often are derived from the nonionic types which include carboxylic acid functions. Alkaline agents are employed to neutralize the carboxylic acid or anhydride transforming them into anionic salts. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). Most preferred is AMP.

Particularly preferred anionic polymers are the salts of poly(methyl vinyl ether/maleic anhydride) and polystyrene sulfonic acid. The former is obtained by at least partial neutralization of Gantrez® S-97 BF and the latter available from the National Starch & Chemical Company under the trademarks Versa TL-501 and Flexan® 130 having respective molecular weights of about 500,000 and 100,000. Other polymer films which may be employed and are commercially available are listed in the Table below.

Cationic amphoteric film-forming polymers suitable for the present invention may be prepared as homo- or copolymers from monomers including:

Dimethyl aminoethyl acrylate (DMAEA), Dimethylaminoethyl methacrylate (DMAEMA), Dimethylaminopropylacrylamide (DMAPAAm), and Dimethylaminopropyl methacrylamide (DMAPMAAm) which are all (meth)acrylamides or (meth)acrylic acid esters having a diallkylamino group;

Dimethylaminostyrene (DMASt) and Dimethyaminomethylstyrene (DMAMSt) and the like which are styrenes having a dialkylamino group;

4-Vinyl pyridine and 2-vinyl pyridine which are vinyl pyridines; and

Quaternized products of these with a known quaternizing agent such as alkyl halide, benzyl halide, alkyl or aryl sulfonic acid, or dialkyl sulfate.

Among suitable film-forming polymers are those derived from monomers such as:

N-(3-sulfopropyl)-N-acryloyloxyethyl-N,N-dimethylammonium betaine, N-(3-sulfopropyl)-N-methacroylamidepropyl-N ,N-dimethylammonium betaine, N-(3-carboxymethyl)-N-methacroylamidepropyl-N, N-dimethylammonium betaine and N-carboxymethyl-N-methacroyloxyethyl-N,N-dimethylammonium betaine.

The most preferred polymers for use in the present invention are chemically modified cellulosics, especially methyl cellulose, hydroxypropyl methylcellulose, methyl cellulose, ethyl cellulose, hydroxypropyl cellulose, hydroxypropyl methyl cellulose, sodium carboxymethyl cellulose and combinations thereof available under the Methocel® brand from the Dow Chemical Company.

Amounts of the film-forming polymer may range from about 0.0001 to about 10%, preferably from about 0.01 to about 5%, more preferably from about 0.1 to about 3%, optimally from about 0.25 to about 0.75% by weight of the absorbent covering.

The treatment composition relative to the fibrous absorbent covering will have a weight ratio ranging from about 100:1 to about 1:100, preferably from about 20:1 to about 1:20 by weight.

Optionally, active agents may be included within the treatment compositions. Suitable active agents for the present invention include anti-microbial agents, anti-inflammatory agents, antiseptic agents, anaesthetic agents, anti-acne agents, anti-irritant agents and combinations thereof.

Illustrative anti-microbial agents (antibacterial, antifungal, anti-protozoal and antiviral) are beta-lactams, quinolones, ciprofloxacin, norfloxacin, tetracycline, erythromycin, amikacin, doxycycline, capreomycin, chlorhexidine, chlortetracycline, oxytetracycline, clindamycine, ethambutol, metronidazole, pentamidine, gentamicin, kanamycin, lineomycin, methacycline, methenamine, minocycline, neomycin, netilmicin, paromomycin, streptomycin, tobramycin, miconazole, amanfadine, clindamycin and cephalosporin. Anti-microbial agents preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, penamidine hydrochloride, gentamicin sulfate, kamaycin sulfate, lineomycin hydrochloride, methacryline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, p-chloro-m-xylenol, nystatin, tolnafate and clotrimazole. Most preferred are polymyxin B sulfate, neomycin and bacitracin (particularly zinc bacitracin).

Illustrative anti-inflammatory agents are aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory agents including hydrocortisone.

Antiseptic agents suitable for the present include phenoxyisopropanol, resorcinol, chlorhexidine, hydrogen peroxide, organic $C_2$–$C_{30}$ peroxides, povidone and iodine.

Anaesthetic agents suitable for the present invention include benzocaine, lidocaine, bupivacaine, chlorprocaine, dibucaine, etidocaine, mepivacaine, tetracaine, dyclonine, hexylcaine, procaine, cocaine, ketamine, pramoxine, phenol and pharmaceutically acceptable salts thereof.

Anti-acne agents include alpha-hydroxy carboxylic acids (e.g. glycolic acid, lactic acid and gluconolactone), beta-hydroxy carboxylic acids (e.g. salicylic acid), benzoyl peroxide, sulfur, retinoids (e.g. retinol and retinoic acid) and combinations thereof.

Anti-irritant agents suitable for the present invention include alpha-bisabolol, farnesol, chamomile extract, phytic acid, and glycyrrhetinic acid and salts thereof.

Amounts of the active agents will depend on their activity. Generally, amounts of any active may range from about 0.0000001 to about 20%, preferably from about 0.000001 to about 10%, more preferably from about 0.00001 to about 5%, particularly preferably from about 0.01 to about 1%, even more preferably from about 0.1 to about 0.5% by weight of the treatment composition.

A pharmaceutically or cosmetically acceptable carrier will also be necessary for delivery of the active agent. Carriers may either be hydrophilic or hydrophobic, although the latter are much preferred.

Typical hydrophilic carriers include polyhydric alcohols and polyalkoxylated ethers and esters.

Representative of polyhydric alcohols are glycerin, propylene glycol, dipropylene glycol, polypropylene glycol, polyethylene glycol, sorbitol, hydroxypropyl sorbitol, hexylene glycol, 1,3-butylene glycol, 1,2,6-hexanetriol, fructose, mannose and combinations thereof.

Representative polyalkoxylated ethers and esters include ethoxylated glycerin, propoxylated glycerin, ethylene glycol mono- and di- $C_8$–$C_{22}$ fatty acid esters, polyethylene glycol mono- and di- $C_8$–$C_{22}$ fatty acid esters, polypropylene glycol mono- and di- $C_8$–$C_{22}$ fatty acid esters, glyceryl mono- and di- $C_8$–$C_{22}$ fatty acid esters, ethoxylated glyceryl monostearate, butylene glycol distearate, sorbitan $C_8$–$C_{22}$ fatty acid esters, polyoxyethylene sorbitan $C_8$–$C_{22}$ fatty acid esters and combinations thereof.

Hydrophobic carriers include silicone oils/gums; hydrocarbons; fatty alcohols; mono-, di and tri-glycerides; and fatty acids and esters thereof including waxes.

Among the preferred silicones are polyalkyl siloxanes, polyalkylaryl siloxanes, polyether siloxane copolymers and combinations thereof. Average number molecular weights may range from about 100 to about 5,000,000. The silicones may be grafted and/or crosslinked. The latter may form silicone elastomers such as Polysilicone-11.

Hydrocarbons include mineral oil, isoparaffin, petrolatum, paraffin wax, polyalphaolefin, squalane and squalene, polybutene, microcrystalline polyethylene wax and combinations thereof.

Representative esters include $C_2$–$C_{40}$ alkenyl or alkyl esters of fatty acids. Examples include isoarachidyl neopentanoate, isononyl isonanoate, oleyl myristate, oleyl stearate, oleyl oleate and combinations thereof. Wax esters may also be included such as beeswax, spermaceti and arachidyl behenate. Sterol esters are suitable including cholesterol fatty acid esters.

Fatty acids and fatty alcohols, each having from 8 to 30 carbon atoms may be included as a hydrophobic pharmaceutically acceptable carrier. Representative of the fatty acids are lauric, myristic, palmitic and stearic acids. Representative of the fatty alcohols are lauryl, palmityl, stearyl, isostearyl and cetearyl alcohols.

Amounts of any of the carriers may range from about 1 to about 99.9%, preferably from about 80 to about 99.9%, optimally from about 95 to about 99% by weight of the treatment composition.

Viscosity of the treatment composition should range from about 50 cps to about 5 million cps, preferably from about 100,000 to about 3,500,000 cps, more preferably from about 800,000 to about 2,500,000 cps, optimally from about 1,000,000 to about 2,000,000 cps, as measured with a Brookfield DV-1+ Viscometer at 25° C. using a TF Spindle rotating at 5 rpm. This measurement is via descending heliopath for one minute, using a factor of 20,000 to convert to cps units.

Swabs of the present invention are preferably loaded with a hydrophobic oleaginous treatment composition. More particularly, the oleaginous treatment composition utilizes a carrier combination of mineral oil and petrolatum. Antimicrobial agents such as bacitracin are supported within the oleaginous treatment composition. The resultant thick carrier/active system is deposited onto the cotton absorbent covering at the end of a plastic stick. The combination is then placed within a laminated foil pouch with the perimeter sealed to prevent any contamination of the contents. When needed, the sealed pouch can be broken (most easily at a tear arrow along a line of package weakness) and the ointment treated cotton tip applied to an open wound as first aid treatment against infection.

Except where otherwise explicitly indicated, all numbers in this description indicating amounts of material ought to be understood as modified by the word "about". All parts, percentages and proportions referred to herein and in the appended claims are by weight unless otherwise indicated.

The term "comprising" is meant not to be limiting to any subsequently stated elements but rather to encompass non-specified elements of major or minor functional importance. In other words the listed steps, elements or options need not be exhaustive.

The foregoing description illustrates selected embodiments of the present invention. In light thereof variations and modifications will be suggested to one skilled in the art, all of which are within the spirit and purview of this invention.

What is claimed is:

1. A swab product comprising:
   (i) an elongate stem with first and second ends opposite one another, a fibrous absorbent covering surrounding at least one of the first and second ends, the covering being impregnated with and held together by a film-forming polymer; and
   (ii) a treatment composition comprising an active agent and from about 80 to about 99.9% of a hydrophobic carrier, the composition deposited onto the film-forming polymer impregnated covering and having a viscosity ranging from about 50 cps to about 5,000,000 cps.

2. The product according to claim 1 wherein the-carrier is selected from the group consisting of mineral oil, petrolatum, paraffin wax, isoparaffin, potyalphaolefin, polybutene, microcrystalline polyethylene wax and combinations thereof.

3. The product according to claim 1 wherein the absorbent covering comprises cotton.

4. The product according to claim 1 wherein the film-forming polymer is a chemically modified cellulose polymer.

5. The product according to claim 4 wherein the chemically modified cellulose polymer is selected from the group consisting of methyl cellulose, ethyl cellulose, hydroxypropyl cellulose, hydroxypropyl methyl cellulose, sodium carboxymethyl cellulose and combinations thereof.

6. The product according to claim 1 wherein the active agent is selected from the group consisting of anti-microbial agents, anti-inflammatory agents, antiseptic agents, anaesthetic agents, anti-acne agents, anti-irritant agents and combinations thereof.

7. The product according to claim 1 wherein the treatment composition has a viscosity ranging from about 800,000 cps to about 2,500,000 cps.

8. A swab product comprising:
   (i) an elongate stem with first and second ends opposite one another, a fibrous cellulosic absorbent covering surrounding at least one of the first and second ends, the covering being held together by a film-forming polymer in an amount from about 0.0001 to about 10% by weight of the covering; and
   (ii) a treatment composition comprising from about 0.0000001 to about 20% by weight of the composition of an active agent and from about 80 to about 99.9% by weight of the composition of a cosmetically acceptable carrier, the composition having a viscosity ranging from about 100,000 to about 3,500,000 cps.

9. A method for treating diseased or injured skin comprising applying to the skin through aid of a swab a treatment composition via a swab product comprising:
   (i) an elongate stem with first and second ends opposite one another, a fibrous absorbent covering surrounding at least one of the first and second ends, the covering being impregnated with and held together by a film-forming polymer in an effective amount to prevent the covering from unfurling during use; and
   (ii) a treatment composition comprising an active agent dispersed in from about 80 to about 99.9% of a hydrophobic carrier, the composition deposited onto the film-forming polymer impregnated covering and having a viscosity ranging from about 100,000 cps to about 5,000,000 cps.

* * * * *